(12) United States Patent
Yau

(10) Patent No.: US 10,851,338 B2
(45) Date of Patent: Dec. 1, 2020

(54) BIO-REACTIVE SYSTEM AND METHOD FOR VOLTAGE CONTROLLED METABOLISM

(71) Applicant: Siu-Tung Yau, Solon, OH (US)

(72) Inventor: Siu-Tung Yau, Solon, OH (US)

(73) Assignee: Siu-Tung Yau, Solon, OH (US)

( * ) Notice: Subject to any disclaimer, the term of this patent is extended or adjusted under 35 U.S.C. 154(b) by 11 days.

(21) Appl. No.: 16/045,903

(22) Filed: Jul. 26, 2018

(65) Prior Publication Data

US 2019/0024035 A1  Jan. 24, 2019

Related U.S. Application Data

(62) Division of application No. 15/109,891, filed as application No. PCT/US2015/010248 on Jan. 6, 2015, now abandoned.

(Continued)

(51) Int. Cl.
*C12M 1/42* (2006.01)
*G01N 33/483* (2006.01)
(Continued)

(52) U.S. Cl.
CPC .............. *C12M 35/02* (2013.01); *C12M 1/42* (2013.01); *C12M 23/20* (2013.01); *C12N 13/00* (2013.01);
(Continued)

(58) Field of Classification Search
CPC ........ C12M 35/02; C12M 1/42; C12M 23/20; C12N 13/00; C12P 7/06; Y02E 50/17; G01N 33/483
See application file for complete search history.

(56) References Cited

U.S. PATENT DOCUMENTS 8,585,879 B2 * 11/2013 Yau .................... G01N 27/3277
  204/403.01
9,605,295 B2 * 3/2017 Yau ........................ C12Q 1/26
(Continued)

OTHER PUBLICATIONS

Aagapakis, Christina M., et al. "Insulation of a synthetic hydrogen metabolism circuit in bacteria." Journal of biological engineering 4.1 (2010): 3.

(Continued)

*Primary Examiner* — William H. Beisner
*Assistant Examiner* — Danielle B Henkel
(74) *Attorney, Agent, or Firm* — Tarolli, Sundheim, Covell & Tummino LLP

(57) ABSTRACT

Bio-reactive systems for voltage controlled metabolism are described, that include electrochemical-electrostatic systems having a conventional three electrode cell modified with at least one additional gating electrode. The rate of a metabolic process occurring in at least one organism disposed on a working electrode is controllable by applying a gating voltage VG to the at least one gating electrode. A method for voltage controlled metabolism in a bio-reactive electrostatic cell that includes applying a gating voltage VG to at least one gating electrode is also described. The rate of a metabolic process may be controlled by altering at least one of the magnitude and polarity of the applied gating voltage VG. The method for voltage controlled metabolism may further be used to treat cancer and/or increase the rate of ethanol production by fermentation.

11 Claims, 15 Drawing Sheets

Related U.S. Application Data

(60) Provisional application No. 61/924,072, filed on Jan. 6, 2014.

(51) Int. Cl.
  *C12N 13/00* (2006.01)
  *C12P 7/06* (2006.01)
  *C12M 1/00* (2006.01)
  *G01N 33/487* (2006.01)

(52) U.S. Cl.
  CPC .............. *C12P 7/06* (2013.01); *G01N 33/483* (2013.01); *G01N 33/48707* (2013.01); *Y02E 50/17* (2013.01)

(56) References Cited

U.S. PATENT DOCUMENTS

| | | | |
|---|---|---|---|
| 2008/0305471 | A1 | 12/2008 | Carmeli et al. |
| 2009/0093037 | A1 | 4/2009 | Kim et al. |
| 2012/0267255 | A1 | 10/2012 | Yau |
| 2016/0333301 | A1* | 11/2016 | Yau .................. C12M 35/02 |

OTHER PUBLICATIONS

Choi, Yongki, and Siu-Tung Yau. "Field-effect enzymatic amplifying detector with picomolar detection limit." Analytical chemistry 81.16 (2009): 7123-7126.

Choi, Yongki, and Siu-Tung Yau. "Field-controlled electron transfer and reaction kinetics of the biological catalytic system of microperoxidase-11 and hydrogen peroxide." AIP Advances 1.4 (2011): 042175.

Davies, Paul, Lloyd A. Demetrius, and Jack A. Tuszynski. "Implications of quantum metabolism and natural selection for the origin of cancer cells and tumor progression." AIP advances 2.1 (2012): 011101.

Dzyadveych, Sergei V., et al. "Biosensors based on enzyme field-effect transistors for determination of some substrates and inhibitors." Analytical and Bioanalytical Chemistry 377.3 (2003): 496-506.

Jackson, John David. Classical electrodynamics. John Wiley & Sons, 2012.

Song, Yang, Jiapeng Wang, and Siu-Tung Yau. "Controlled glucose consumption in yeast using a transistor-like device." Scientific reports 4 (2014): 5429.

Yau, Siu-Tung, et al. "Voltage-controlled enzyme-catalyzed glucose—gluconolactone conversion using a field-effect enzymatic detector." Physical Chemistry Chemical Physics 15.46 (2013): 20134-20139.

Zhao, Yuhua, Ethan B. Butler, and Ming Tan. "Targeting cellular metabolism to improve cancer therapeutics." Cell death & disease 4.3 (2013): e532.

PCT International Search Report and Written Opinion for corresponding International Application No. PCT/US2015/010248, dated Mar. 31, 2015, pp. 1-13.

Extended European Search Report for corresponding EP App. No. 15733148.9 dated Dec. 22, 2016, pp. 1-6.

* cited by examiner

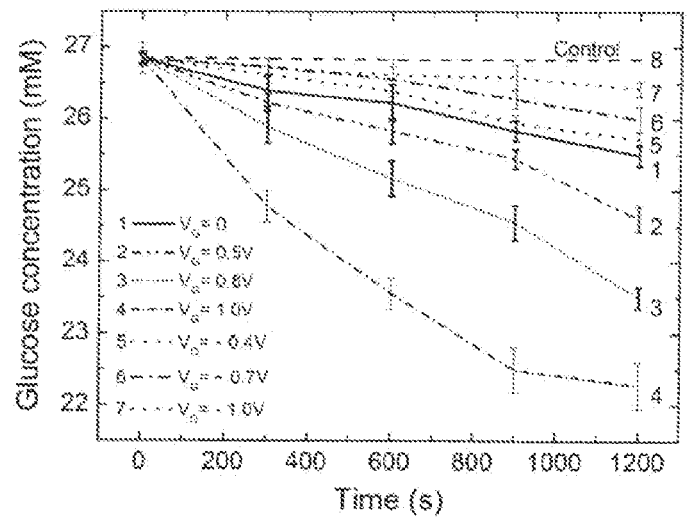
(a)
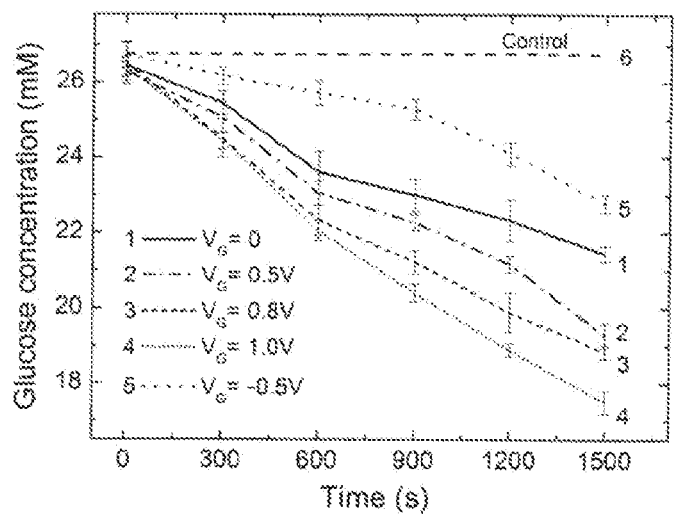
(b)
FIG. 6 a,b

BIO-REACTIVE SYSTEM AND METHOD FOR VOLTAGE CONTROLLED METABOLISM

CROSS-REFERENCE TO RELATED APPLICATIONS

This application is a Divisional of U.S. patent application Ser. No. 15/109,891, filed on Jul. 6, 2016, which is a U.S. National Stage application under 35 USC 371 of PCT application Ser. No. PCT/US2015/010,248, filed on Jan. 6, 2014, which claims priority to U.S. Provisional Application Ser. No. 61/924,072, filed on Jan. 6, 2014, which is hereby incorporated by reference in its entirety.

BACKGROUND

The present application generally relates to an electrochemical-electrostatic bio-reactive system and method thereof for voltage controlled metabolism. The electrochemical system generally relates to, but is not limited to, amperometry, cyclic voltammetry (CV), linear voltammetry, pulse voltammetry, and the like. The electrostatic system consists of two electrodes connected via a voltage source, wherein one electrode is coated with an insulating material so that no electric current flows in this circuit. In exemplary embodiments, an electrochemical-electrostatic bio-reactive system applies a voltage to an electrochemical cell in order to control the kinetics of a metabolic reaction taking place in a single organism or organisms in the cell. In other exemplary embodiments, a method of controlling a metabolic reaction caused by a single organism or organisms includes altering a voltage applied within an electrochemical cell.

Glucose metabolism is the most important and widely studied form of carbohydrate metabolism. Glucose metabolism in cells generates energy for living systems to sustain biological functions. The term "glucose metabolism" generally refers to the cellular processes that convert glucose to energy for cell utilization. There has been a recent renewed interest in glucose metabolism due its central role in areas of cell biology, physiology, medicine and synthetic biology. Effective control of cellular glucose metabolism has many important future implications, e.g., in developing new cancer therapies and for synthesizing biofuels from organisms.

An emerging theme in cancer research is that metabolic regulation, particularly dealing with glucose metabolism, is intricately linked to cancer formation and progression. The Warburg effect has shown that, compared with normal cells, cancer cells consume much more glucose and mainly process it through aerobic glycolysis. Zhao, Y., Butler, E. B., and Tan, M., *Cell Death and Disease* 4, e532; doi:10.1038/cddis.2013.60 (2013). Additionally, the theory of quantum metabolism has shown that a difference in metabolic rate exists between normal cells and cancer cells using electron transit times (which describes the turnover time of redox reactions). Davies, P., Demetrius, L. A., and Tuszynski, J. A., *AIP Advances* 2, 011101 (2012). This recognized difference in the rate of glucose consumption between normal cells and cancer cells shows that altering the rate of glucose metabolism, e.g. lowering the rate of glucose consumption in cancer cells, may be used in new cancer therapies. Metabolic engineering has also turned towards methods of controlling metabolism for the production of important biofuels. For example, cellular metabolic pathways in yeast or bacteria may be controlled to synthesize compounds or fuels that are difficult or expensive to produce by other means.

There is presently a dearth of methods for facile control of metabolism. Present methods of controlling metabolism are expensive and/or require an undue amount of time to conduct. Accordingly, an unmet need exists for new cancer therapies and accelerated fermentation processes of making biofuels such as ethanol based on the control of metabolic processes. Such methods would preferably enable cancer research and prevention methods and/or cheap production of biofuels by controlling the rate of metabolism in a relatively quick and cost-effective manner.

SUMMARY

The present application provides systems and methods for controlling the kinetics of metabolism by using a voltage source that applies a voltage to an electrically insulated electrode(s) without causing a current in its own circuit. The systems and methods may be used, e.g., in the production of alcoholic beverages and ethanol for fuel and/or industrial use, in the production of other biofuels and biomolecules, in medical research, treatment and imaging, or in food processing applications that involve fermentation. Future applications of the disclosed systems and methods may include controlling any of the differing forms of metabolism in a single organism or organisms in a container.

More specifically, a diagnostic and treatment method for cancer based on the Warburg effect may be conducted using the disclosed systems and methods. Additionally, the disclosed systems and methods can be used to control cellular production of many useful substances including biofuels and ethanol.

In one aspect, the present invention provides an electrochemical-electrostatic bio-reactive system for voltage controlled metabolism according to a first exemplary embodiment comprises a working electrode, a reference electrode, and a counter electrode connected in a conventional three electrode electrochemical cell. The reference electrode and the counter electrode may be combined in a single electrode. The system further includes a gating electrode connected to an external voltage source. The gating electrode may include a piece of metal operating as a conductor, where the metal is coated with an insulator so that the metal is not exposed to the solution in the electrochemical cell. The metal may be connected through the external voltage source to the working electrode. An organism or organisms are placed in physical contact with the working electrode. The organism or organisms are operative to cause metabolism of at least one metabolic substrate disposed on the organism or organisms. The kinetics of the metabolism is controlled by applying a gating voltage $V_G$ via the external voltage source between the gating electrode and the working electrode, which is in contact with the organism or organisms. A rate of the transfer of electrons via/through or within the organism or organisms may be controllable by applying a gating voltage $V_G$ between the gating electrode and the working electrode, which is in contact with the organism or organisms.

Another aspect of the invention provides an electrochemical-electrostatic bio-reactive system for voltage controlled metabolism including a first electrode, a second electrode, and at least one organism. The at least one organism may be immobilized on or in physical contact with the first electrode. The at least one organism may also be suspended in a solution in the presence of the first electrode and second electrode without being immobilized on or in physical contact to the electrodes. The second electrode consists of a piece of metal/conductor, which is coated with an insulator, the metal/conductor being electrically connected via a voltage source to the first electrode, which may consist of a piece of metal/conductor, which may be coated with an insulator. The coating insulators prevent the metals of the electrodes from being exposed to the solution contained in the system.

A method for voltage controlled metabolism in an electrostatic bio-reactive cell according to an exemplary embodiment comprises disposing at least one organism on a first electrode or dissolving at least one organism in a solution in the presence of a first electrode and a second electrode with either or both electrode coated with an insulator, contacting the at least one organism with at least one substrate present in a solution, applying a gating voltage $V_G$ to one or more second electrodes, which is coated with an insulator, disposed within the solution and electrically connected to the first electrode via the voltage source $V_G$, and controlling a rate of a metabolic reaction caused by the at least one organism by selecting at least one of the magnitude and polarity of the applied gating voltage $V_G$.

A method for diagnosing, treating or studying cancer with a voltage controlled bio-reactive electrochemical-electrostatic cell or the like comprises placing in contact with or immobilizing a tumor tissue on a working electrode, applying a gating voltage $V_G$ to one or more gating electrodes, which is coated with an insulator and electrically connected to the working electrode via the voltage source $V_G$; and changing the rate of tumor tissue formation by applying a gating voltage $V_G$.

A method for forming ethanol with a voltage controlled electrochemical-electrostatic bio-reactive cell comprises immobilizing or making contact with a yeast cell on a working electrode, contacting the yeast with a glucose or sugar solution, applying a gating voltage $V_G$ to one or more gating electrodes, which is coated with an insulator and disposed within the solution and electrically connected via a voltage source to the working electrode; and changing the rate of fermentation caused by the yeast cell by applying a gating voltage $V_G$.

BRIEF DESCRIPTION OF THE FIGURES

The accompanying drawings, which are incorporated in and constitute a part of this specification, illustrate some embodiments disclosed herein, and together with the description, serve to explain principles of the disclosed embodiments.

FIG. 6(a) is a graph of glucose concentration (mM) v. time (s) obtained on the system of FIG. 1 under aerobic conditions. Curves 1-4 show a decrease in glucose concentration at progressively faster rates as the amount of $V_G$ is increased. Curves 5-7 show a progressively slower rate of decreasing glucose concentration as the polarity of $V_G$ is reversed. Curve 8 is a control trace obtained using a bare electrode. The curves were obtained at room temperature.

FIG. 6(b) is a graph of glucose concentration (mM) v. time (s) obtained on the system of FIG. 1 under anaerobic conditions. Curves similar to those illustrated FIG. 5(a) were achieved, however the anaerobic process in FIG. 6(b) shows faster depletion rates for glucose than those in the aerobic process in FIG. 6(a). The curves were obtained at room temperature.

DETAILED DESCRIPTION

Figure 1:
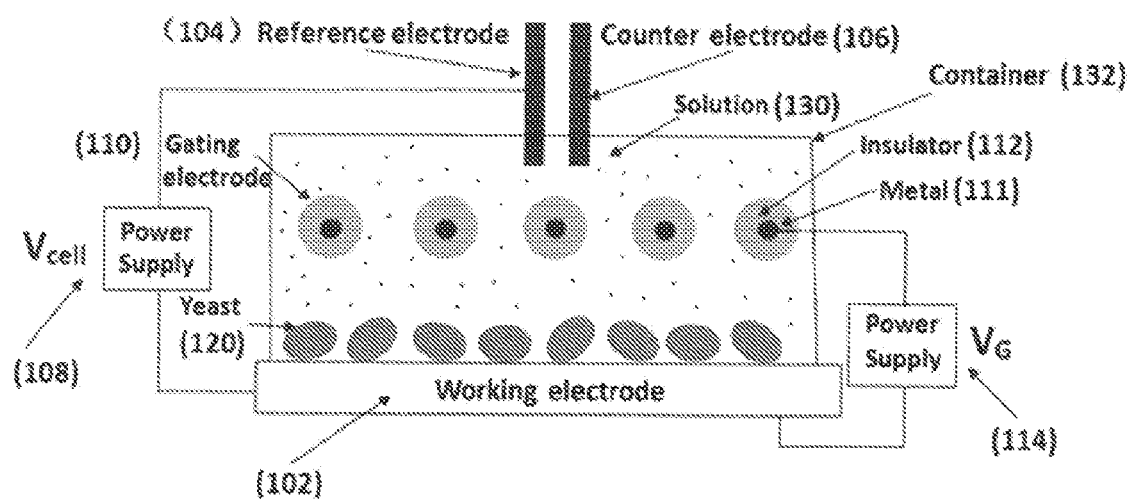
FIG. 1 is a diagram of an electrochemical-electrostatic system for voltage controlled metabolism according to a first exemplary embodiment. A conventional three-electrode electrochemical cell is modified with one or more additional gating electrodes for applying a gating voltage $V_G$ to the working electrode, upon which yeast cells are immobilized. $V_{cell}$ is the cell potential. The gating voltage $V_G$ can be altered in order to control the rate of glucose or other sugars metabolism in the yeast cells. The gating electrodes are electrically connected.

The present application provides a bio-reactive systems for voltage controlled metabolism and methods for using the systems. The bio-reactive system can include an electrostatic-electrochemical system including a conventional three electrode electrochemical cell, or the bio-reactive system can include an electrostatic system including a first and second electrode(s).

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It must be noted that as used herein and in the appended claims, the singular forms "a", "and", and "the" include plural referents unless the context clearly dictates otherwise. Thus, for example, reference to "an organism" includes a plurality of organisms.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values; however, inherently contain certain errors necessarily resulting from error found in their respective measurements.

The present application provides a bio-reactive systems for voltage controlled metabolism and methods for using the systems. The bio-reactive system can include an electrostatic-electrochemical system including a conventional three electrode electrochemical cell, or the bio-reactive system can include an electrostatic system including a first and second electrode.

In one aspect, the present invention provides an electrochemical-electrostatic bio-reactive system for voltage controlled metabolism that includes a working electrode, a reference electrode, and a counter electrode connected in a conventional three electrode electrochemical cell; at least one gating electrode comprising a metal coated with an insulator, the gating electrode being electrically connected via an external voltage source, that produces a gating voltage $V_G$ to the working electrode; and at least one organism disposed on the working electrode, the at least one organism operative to cause metabolism of at least one metabolic substrate; wherein the kinetics of the metabolism is controlled by applying a gating voltage $V_G$ via the external voltage source between the gating electrode and the working electrode, which is in contact with the at least one organism.

With reference to FIG. 1, an electrochemical-electrostatic bio-reactive system 100 according to a first exemplary embodiment is illustrated which includes a conventional three-electrode electrochemical cell including a working electrode 102, a reference electrode 104, and a counter electrode 106. The reference electrode 104 is used to control the potential of the working electrode 102 (and the cell current) while current flows between the working electrode 102 and counter electrode 106 through a solution 130 held in container 132. The potential difference/voltage between the working electrode and the reference electrode is controlled by the voltage source $V_{cell}$ or power supply 108.

The term "bio-reactive," as used herein, refers to a system including a bioreactor that supports a biologically active environment. In particular, a bioreactor is a vessel in which a chemical process is carried out which involves organisms or biochemically active substances derived from such organisms. The term "electrostatic," as used herein, refers a stationary electric charge or field as opposed to electric currents. The term "electrochemical," as used herein, refers to a system including a three electrode (working, reference and counter) electrochemical cell.

The conventional three-electrode electrochemical cell of FIG. 1 may be modified with one or more additional gating electrodes 110. The gating electrodes 110 are comprised of metal 111 and coated by an insulator 112. The metal should be a conductive metal such as silver, copper, gold, platinum, or aluminum. Examples of insulating materials that can be used to coat the metal 111 include glass, ceramic, and polymers, such as polyethylene, polystyrene, polypropylene, polyvinyl chloride, nylon, cellulose, and polycarbonate. The one or more gating electrodes 110 are for applying the gating voltage $V_G$ 114 to the working electrode 102. The insulator 112 should be effective to prevent current flow in the gating electrode 110-solution 130-working electrode 102 circuit. A plurality of gating electrodes 110 may be employed with their metal 111 portions electrically connected. The applied gating voltage $V_G$ 114 may be generated by a voltage source as known to one having ordinary skill in the art. The one or more gating electrodes 110, the voltage source $V_G$ or power supply 114 and the working electrode 102 form a separate electrical system relative to the conventional three-electrode cell. Current does not flow in this system because of the insulator 112. In addition, in some embodiments, the reference and counter electrodes are combined into a single electrode.

One or more organisms (e.g., yeast cells) 120 are disposed on the working electrode 102 which interacts with a metabolic substrate (e.g., glucose). Organisms suitable for use in the present invention include cells such as eukaryotic or prokaryotic cells. The cells can be single cells, or they can form part of a colony or tissue. In some embodiments, the organisms are microbial organisms. Examples of suitable organisms include yeast and algae.

The term "disposed," as used herein, refers to organisms that are immobilized on or in contact with an electrode. For example, an organism can be intentionally attached to the electrode. Alternately, the organism can be suspended in a solution and diffuse to the electrode to make temporary or long term contact to the electrode. Typically, the organism is be bound to the electrode by physical adsorption, which involves the attractive interaction due to opposite charges. However, in some embodiments, the organism can be chemically linked to the electrode using methods known to those skilled in the art.

The bio-reactive system can be used to control the rate of metabolism of a metabolic substrate by the organism. A metabolic substrate is a compound capable of being metabolized by the organism. The specific metabolic substrates will therefore vary depending on the particular organism used in the bio-reactive system. Examples of metabolic substrates include fatty acids, oils, and sugars such as glucose, fructose, and galactose. The metabolic substrate may be included in the solution 130 or in any other manner in which it can be metabolized by the organism. The bio-reactive system can be used to control various different types of metabolic reactions. For example, the system can be used to control carbohydrate metabolism, protein metabolism, and photosynthesis, which involves the metabolism of $CO_2$.

The cell potential $V_{cell}$ 108 may be such that electrons enter the working electrode 102 from the yeast cells 120. Movement of electrons between the microorganism and the working electrode is one way in which the present invention differs from the prior art, in which electrons are sent from an electrode to the microorganism via electron mediators (i.e., charge carriers which are intentionally put into solution) to provide energy for the microorganism to carry out their metabolism.

The system 100 allows for independent and electrostatic control of metabolism in organisms 120 by using the gating voltage $V_G$ 114. For example, glucose consumption by yeast cells 120 disposed on the working electrode 102 can be controlled at will (i.e., increased or decreased) using the gating voltage $V_G$ 114. The rate of glucose consumption in the system 100 has been shown to qualitatively correlate with the voltage-controlled production of the end products of glucose ($C_6H_{12}O_6$) metabolism, which are ATP (adenosine triphosphate), ethanol ($C_2H_5OH$), and carbon dioxide ($CO_2$). The correlation between consumption of glucose and formation of end products such as ethanol indicates that system 100 is capable of controlling the kinetics of the glucose metabolism reaction in yeast through the applied gating voltage $V_G$ 114.

The system 100 can also be viewed from a circuit perspective. In this aspect, the invention provides an electrochemical-electrostatic bio-reactive system for voltage controlled metabolism according to another embodiment comprises a first circuit, a second circuit, and at least one organism. The first circuit comprises a working electrode, a reference electrode, and a counter electrode connected in a conventional three electrode electrochemical cell. The second circuit comprises a gating electrode coated with an insulator and electrically connected to the working electrode via an external voltage source. No currents flow in the second circuit. The at least one organism is placed in physical contact with, or immobilized, on the working electrode. The at least one organism is operative to cause metabolism of at least one metabolic substrate disposed on the at least one organism. The kinetics of the metabolism is controlled by applying a gating voltage $V_G$ via the external voltage source between the gating electrode and the working electrode, which is in contact with the organism or organisms. A rate of the transfer of electrons via/through or within the at least one organism may be controllable by applying a gating voltage $V_G$ between the gating electrode and the working electrode, which is in contact with the organism or organisms. $V_G$ may also control the transfer of electrons between the working electrode and the at least one substrate disposed on the at least one organism via the at least one organism.

Without being bound to any particular theory, $V_G$ 114 is the voltage used to electrostatically manipulate the metabolism reaction without causing a current in the gating electrode-working electrode circuit. Depending on factors such as the composition of the working electrode 102, the geometry of the working electrode 102, the nature of the metabolic substrate, and the concentration of the metabolic substrate, $V_G$ generally has a value of from about −20.0 volt to about 20.0 volt.

According to one embodiment, a positive polarity of $V_G$ can be applied to system 100 to increase the kinetics of a metabolic process occurring in an organism 120. According to another embodiment, a negative polarity of $V_G$ may also be applied to system 100 to decrease the kinetics of the metabolic process.

An important aspect of metabolism is cellular electron transport. The feasibility of controlling electron transfer in biological systems using a gating voltage has been demonstrated in the reduction of hydrogen peroxide ($H_2O_2$) at an electrode immobilized with microperoxidase-11, showing controlled kinetics of the bio-catalytic system. Choi, Y. and Yau, S.-T. *AIP Advances* 1, 042175 (2011). Engineered electron transport has also been achieved in *E. coli* to produce hydrogen using elimination of competing reactions, engineering of protein interaction surfaces, and protein fusion or scaffolding. Agapakis, C. M. et al., *Journal of Biological Engineering* 4:3 (2010). Observation on glucose consumption and the production of metabolic end products using the systems described in the present application performed with different magnitudes and polarities of $V_G$ provides evidence that the observed controlling of metabolism described in the present application is due to controlled cellular electron/charge transport. Song, Y., Wang, J., and Yau, S.-T. *Scientific Reports* 4, 5429 (2014).

System 100 may control the rate of glucose consumption or depletion in the presence of yeast (*Saccharomyces cerevisiae*) by using electrostatic means. The gating voltage $V_G$ 114 applied to the working electrode 102 can be used as a parameter for controlling the kinetics of glucose metabolism. Advantageously, various embodiments of system 100 provide a measure of control over metabolism based on a variety of biochemical reactions. System 100 may control metabolism using a voltage source ($V_G$ 114) to control metabolism without dissipating electrical current. Also, system 100 does not require introducing chemicals (mediators)

into the solution containing the substrate and matrix where metabolism takes place. In some embodiments, the system 100 may be contained within a compartment 132.

The system 100 according to a second exemplary embodiment includes the electric circuit between the one or more gating electrodes 110, the voltage source $V_G$ 114 and the working electrode 102, which may be coated with an insulator, however forgoes the voltage source $V_{cell}$ 108 and the other electrodes normally found in a conventional three electrode cell (the reference electrode 104 and counter electrode 106). The electrochemical system is therefore turned off. The at least one organism may be suspended in the solution 130 in the presence of both electrodes. The at least one organism may be in contact with either or both electrode(s). The system 100 according to the second exemplary embodiment is able to control the consumption of a metabolic substrate (e.g., glucose or sugar) and the formation of end products in a metabolic reaction without a current being involved in these processes.

The system 100 can be used to form a variety of different metabolic end products, depending on the organism and the substrate being used. For example, when the organism is yeast and the substrate is a sugar such as glucose, the system can be used to form ethanol as metabolic end product. In some embodiments, the metabolic reaction carried out by the system produces at least one end product suitable for use as a biofuel. Examples of biofuels include hydrogen, alkanes such as methane, and alcohols such as ethanol.

Figure 2:
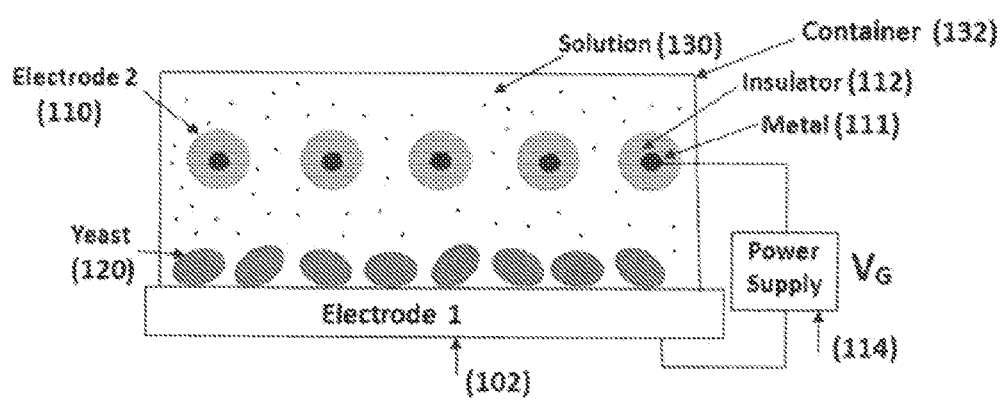
FIG. 2 is a diagram of an electrostatic bio-reactive system for voltage controlled metabolism according to a second exemplary embodiment.

FIG. 2 shows the schematic of the actual system, which includes the electric circuit between the one or more gating (second) electrodes 110 and the working (first) electrode 102, however forgoes the other electrodes normally found in a conventional three electrode cell (the reference electrode 104 and counter electrode 106). The electrochemical system was turned off.

When under the influence of $V_G$, the system 100 of either the first and second exemplary embodiments changes the consumption of glucose based on glucose metabolism performed by the yeast cells 120 in contact with, or immobilized on, the working electrode 102, or the yeast can be suspended in a solution in the container 132. Without being bound to any particular theory, $V_G$ 114-induced altered metabolism may occur based on an electrostatic mechanism. Since the one or more gating electrodes 110 are electrically insulated, the modification produced by $V_G$ 114 to the metabolic processes may be of an electrostatic nature. The different pathways in yeast cells 120 all involve redox reactions catalysed by redox enzymes. For example, the redox reaction of the $NAD^+$/NADH redox couple is catalysed by different dehydrogenases in glycolysis, the Krebs cycle, and the electron transport chain.

Again without being bound by theory, the control of metabolism provided by the systems described herein may be due to the modification of the tunnel barrier for cellular charges; i.e., NAD+ and NADH, by the electric field induced by $V_G$. However, when NAD+ and NADH transfer electrons faster, the organism (e.g., yeast cell) is also being energized at a faster rate so that the cells grow faster. The consumption of glucose and the production of metabolic end products such as ethanol and ATP may therefore occur at a faster rate.

It has been previously demonstrated that a gating voltage can be used to control the electron transfer between a redox enzyme and an electrode. See Choi, Y. and Yau, S.-T. *AIP Advances* 1, 042175 (2011); Choi, Y. and Yau, S.-T., *Anal. Chem.* 81, 7123 (2009). The effect, demonstrated with the glucose oxidase-glucose system and the microperoxidase-$H_2O_2$ system, was attributed to the redistribution of charges at the solution-electrode interface induced by the gating voltage so that an electric field was set up to modulate the electron tunnel barrier, which is the protein network between the active site of the enzyme and the electrode. A similar scenario might also occur in the voltage controlled metabolism of glucose through applied $V_G$ in system 100. The rate of electron transfer associated with various redox enzymes/proteins in the metabolic processes can be modulated by the induced field through $V_G$.

Figure 3:
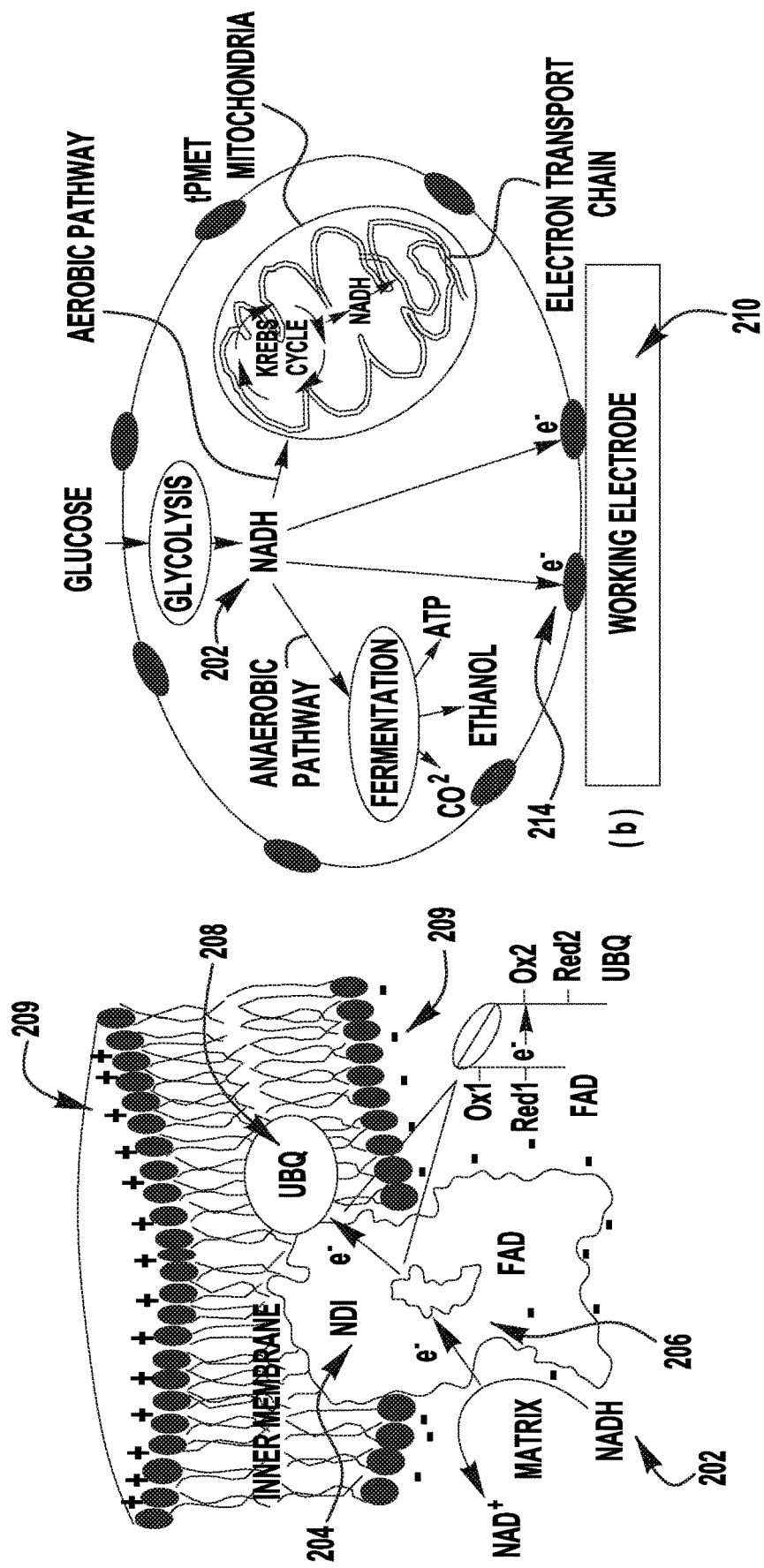
FIG. 3(a) is an illustration of a scenario for the transfer of electrons from NADH to internal NADH dehydrogenase (NDI) and the subsequent tunneling through the enzyme to ubiquinone (UBQ). It is speculated that $V_G$ causes ions to accumulate around the redox enzyme (oxidoreductase) NDI to induce an electric field that penetrate the enzyme and therefore to modulate the height of the tunnel barrier between FAD, the active site of NDI, and UBQ. "ox" and "red" respectively are the oxidized and the reduced energy levels of FAD and UBQ. This is only an example of many interactions between the electron carrier NADH and enzymes in metabolic pathways.
FIG. 3(b) is an illustration of an altered metabolic pathway in yeast cells which are in contact with the working electrode.

With reference to FIG. 3(*a*), a schematic diagram shows the passing of electrons from NADH 202 to the yeast's internal NADH dehydrogenase (NDI) 204 situated in the electron transport chain and the subsequent traversing of the electrons through the FAD center 206 to the ubiquinone (UBQ) 208. FIG. 3(*a*) further shows the $V_G$-induced charges 209 around the enzyme. The induced charges 209 set up an electric field, whose component opposite to the electron's movement through the tunnel barrier of the enzyme modulates the effective height of the barrier so that the electron transfer rate can be increased or decreased. See Jackson, J. D., *CLASSICAL ELECTRODYNAMICS*, 3$^{rd}$ ed., 1998.

Similar modulated electron transfer may also occur with other redox enzymes/proteins involved in the metabolic process, leading to faster production of end products. Accordingly, organisms other than yeast may be used in the system and end product formation of these enzymes may be controlled through applied $V_G$.

With reference to FIG. 3(*b*), a possible description for $V_G$-induced metabolism of glucose in yeast is presented. Since the thickness of the cell wall in yeast cells 120 is about 100-200 nm, the extracellular electron transfer may require a special mechanism. Among the several special mechanisms that have been proposed for extracellular electron transfer, the direct transfer of electrons via the interaction between intracellular electron carriers such as NADH and the trans-plasma membrane electron transfer (tPMET) system 212, a set of redox enzymes and proteins located in the plasma membrane, may be the most relevant for understanding the mechanism of $V_G$-induced metabolism of glucose. The tPMET system consists of cytochromes and various redox enzymes such as NADH oxidase, providing redox activity of the membrane at specific sites.

The transfer of electrons to the working electrode 210 observed in the system 100 of FIG. 1 implies possible altered routes for NADHs 202. With continuing reference to FIG. 3(*b*), possible altered metabolic pathways for the aerobic and anaerobic cases are illustrated. After being generated in glycolysis, instead of diffusing to mitochondria, NADH 202 may diffuse to the plasma membrane, where they pass an electron 214 to the working electrode 210 via the tPMET system 212.

Therefore, in the aerobic case, a fraction of the total NADH 202 deviates from the normal pathway by diffusing to the cell wall, while the remaining NADH 202 diffuses toward mitochondria to maintain the redox balance needed for sustaining the regular metabolic activity of the cell. In the anaerobic case, the amount of NADH 202 that goes to the fermentation process is reduced due to cell wall-bound NADH 202. The diminished amount of NADH 202 that participates in the normal glucose metabolisms does not necessarily result in reduced production of end products. The amount of the end-products produced in system 100 under the influence of $V_G$ is greater than the normal amount. The $V_G$-induced increase of metabolic end products may be due to the enhanced electron transfer occurring in glycolysis and Kreb's cycle, and along the electron transport chain. Therefore, $V_G$ controls the kinetics of the metabolic pathways.

Accordingly, the gating voltage $V_G$ can be used in system 100 as a parameter for controlling the kinetics of glucose metabolism. This technique of applying $V_G$ to alter the rate of metabolic processes may find applications in cancer research and diagnosis and in metabolic engineering, where the kinetics of the production of substances can be controlled using a voltage.

Figure 4:
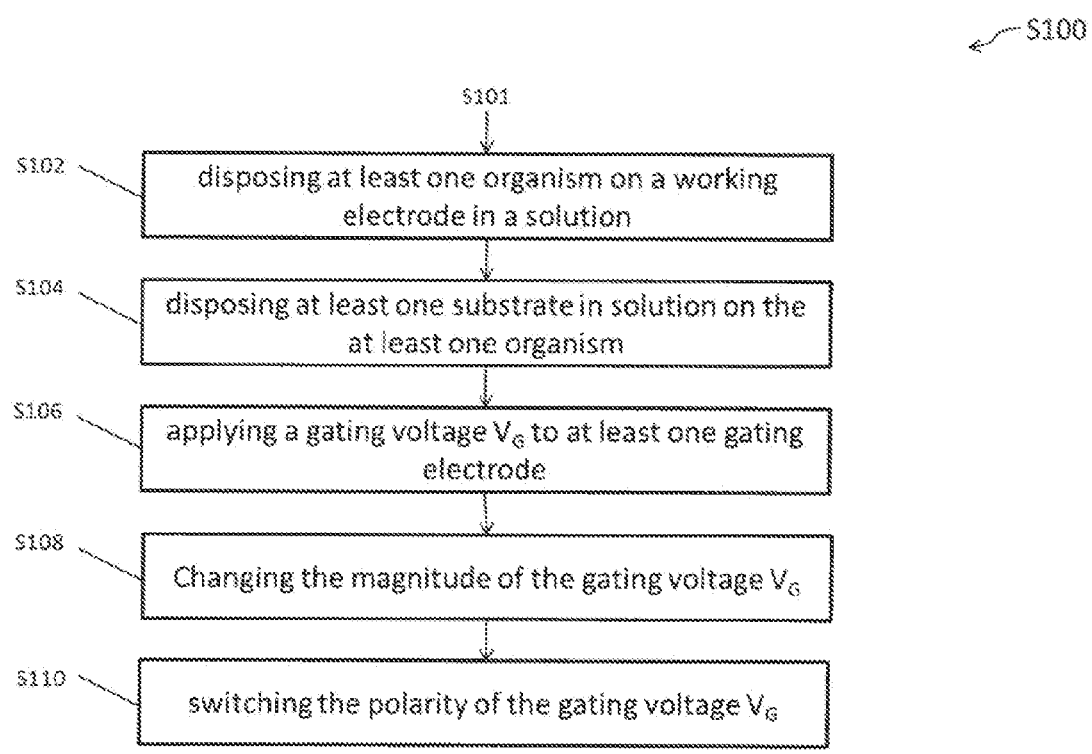
FIG. 4 is a flow chart illustrating a method for voltage controlled metabolism according to an exemplary embodiment.

With reference to FIG. 4, a method S100 for voltage controlled metabolism is illustrated, starting at S101. At S102, at least one organism is immobilized on or in contact with a first electrode in a solution 130. Without being intentionally immobilized or in contact to any electrode, the at least one organism may also be suspended in a solution 130 in the presence of the first electrode and other relevant electrodes, including a second electrode, which is coated with an insulator and electrically connected via a voltage source $V_G$ to the first electrode. According to one embodiment, the at least one organism includes yeast cells. According to another embodiment, the first electrode is a working electrode 102.

The first electrode may or may not be part of a conventional three electrode electrochemical cell. According to one embodiment, the first electrode is a working electrode 102 contained within a conventional three electrode electrochemical cell. According to another embodiment, the electrochemical system of the electrochemical-electrostatic system is turned off and the first electrode, which may be coated with an insulating material, is connected via a voltage source $V_G$ to the second electrode.

At S104, at least one substrate specific for the at least one organism is disposed in a solution 130 so that the at least one substrate is disposed on the at least one organism. The solution 130 may be held within a container 132.

At S106, a gating voltage $V_G$ 114 is applied to one or more second electrodes disposed within the solution 130 and electrically connected via a voltage source 114 to the working electrode 102. According to one embodiment, the one or more second electrodes are gating electrodes 110.

At S108, the magnitude of the gating voltage $V_G$ is changed in order to activate the effect of $V_G$ on the metabolic process caused by the at least one organism. At S110, the polarity of the gating voltage $V_G$ is switched in order to change the normal rate of the metabolic process caused by the at least one organism.

Steps S108 and S110 may be performed separately or in combination to provide complex control over the rate of a metabolic process.

This technique may find applications in cancer research and diagnosis and in metabolic engineering, where the kinetics of the production of substances can be controlled using a voltage. In fact, the $V_G$-controlled ethanol production using system 100 shows a possible role for external voltage in metabolic engineering.

A method S200 according to another embodiment may be adapted for research, the diagnosis or the treatment of cancer based on the Warburg effect. The same principles described in the method S100 would be applied to cancer tumor tissues disposed in a solution. $V_G$ would be adjusted to change the rate of metabolism of glucose within cancer tumor tissues.

A method S300 according to another embodiment may be adapted for the production of ethanol by fermentation. The same principles described in method S100 would apply, however the at least one organism would include yeast cells and the substrate is glucose. According to yet another embodiment, the at least one organism includes other organisms which also produce ethanol by fermentation. The first electrode may or may not be part of a conventional three electrode electrochemical cell.

In some embodiments, the system of the method can be included in a particular device or apparatus. For example, in some embodiments, the system is included in a biosensor. A biosensor is an analytical device, used for the detection of an analyte, that combines a biological component with a physicochemical detector. With regard to the present invention, when the system is included in a biosensor, the biological component can be the organism of the system, while the physicochemical detector is the electrode and other non-organic components of the system. The analyte measured by the system will be the variable factor, while other components of the system are held constant. For example, if the cells and voltage are constant, the system can be used to measure the amount of substrate. A biosensor typically includes associated electronics or signal processors that are primarily responsible for the display of the results in a user-friendly way, and a container for the system and associated electronics and display components.

In another embodiment, the system is included in a biofuel cell. A biofuel cell is a device that converts the chemical energy from biological material that serves as fuel into electricity through a chemical reaction with oxygen or another oxidizing agent. When the system of the invention is included in a biofuel cell, the system of the invention can be used to generate a metabolic end product that is suitable for use as biofuel, which is then burned in a conventional biofuel cell. Alternately, in other embodiments, the electrodes of the system serve as the anode and cathode, which together with the other components of the system, generate direct current electricity such that the system itself acts as a biofuel cell. In some embodiments, a plurality of biofuel cells can be used which are connected in series to provide a desired voltage.

The systems and methods described herein can be applied to a variety of different uses. For example, in one embodiment, the systems can be used for the treatment of wastewater. Wastewater treatment includes conversion of undesirable waste products into less harmful materials, often through the action of microorganisms, and the system and methods of the invention can be used to accelerate this process.

In other embodiments, the system and methods of the invention are used to generate useful metabolic end products. For example, the invention includes methods for performing bioconversion or biotransformation processes to produce biofuels. More specifically, the system and/or method can be used for performing fermentation using yeast or other organisms to produce biofuels, including ethanol. In a related manner, the systems and methods of the invention can be used for performing algae fermentation of sugar to produce oil and biomass. Alternately, or in addition, the system and methods can be used to create food products or alcoholic beverages. In further embodiments, specialized cells can be used to make various specialty biotechnology products. For example, B-cells can be used to make antibodies, and proteins such as enzymes or other proteins can be made from a variety of cells, including recombinant cells.

In other embodiments, the systems and methods of the invention can be used to diagnose, image, or treat diseases involving substrate metabolism, or cellular electron or charge transport. For example, glucose metabolism plays a significant role in cancer, and therefore the systems and methods of the invention can be used to diagnose, image, or treat cancer in a subject. Diseases involving cellular electron or charge transport include mitochondrial disease in relation to other diseases including neurodegenerative conditions (ALS, Alzheimer's, Parkinson's Disease), epilepsy and autism, diseases of the cardiovascular system, liver, and kidney, as well as cancer and diabetes. Alternately, the systems and methods of the invention can be used to modulate other cells or tissue in otherwise healthy individuals. For example, in some embodiments, the system controls the metabolism of red blood cells.

The present invention is illustrated by the following examples. It is to be understood that the particular examples, materials, amounts, and procedures are to be interpreted broadly in accordance with the scope and spirit of the invention as set forth herein.

EXAMPLES

Example 1: An Experimental System for Voltage Controlled Metabolism

As illustrated in FIG. 1, a system for voltage controlled metabolism was constructed using the system 100 according to the first exemplary embodiment. The various steps for construction and operation are detailed below:

Yeast Preparation and Immobilization on the Working Electrode

Dried baker's yeast (Saccharomyces cerevisiae) was purchased from Sigma Aldrich (YSC1) and cultivated for several hours at 30° C. in a solution of deionized water, glucose and peptone. A yeast-immobilized working electrode was prepared by depositing a 0.1 ml drop of the yeast solution on a 1 mm×1 mm area defined using a mask on a pyrolytic graphite (PG) electrode and incubating the electrode at room temperature for 4 hours. Alternatively, yeast can also diffuse to the electrode without immobilization.

Electrochemical Measurements

A conventional three-electrode electrochemical cell with a volume of 2 mL was used to perform electrochemical measurements. The yeast-immobilized electrodes were used as working electrodes. A commercial Ag/AgCl (3 M KCl) electrode was used as the reference electrode and a platinum wire was used as the counter electrode. A piece of 0.5 mm-diameter copper wire coated with a thin layer of insulator (enamel) was used as the gating electrode. The wire was bent to form multiple turns and attached on the working electrode next to the immobilized yeast. The electrochemical cell was driven by a commercial electrochemical controller (CH Instruments 66° C.).

Example 2: Cyclic Voltammetry

Figure 5:
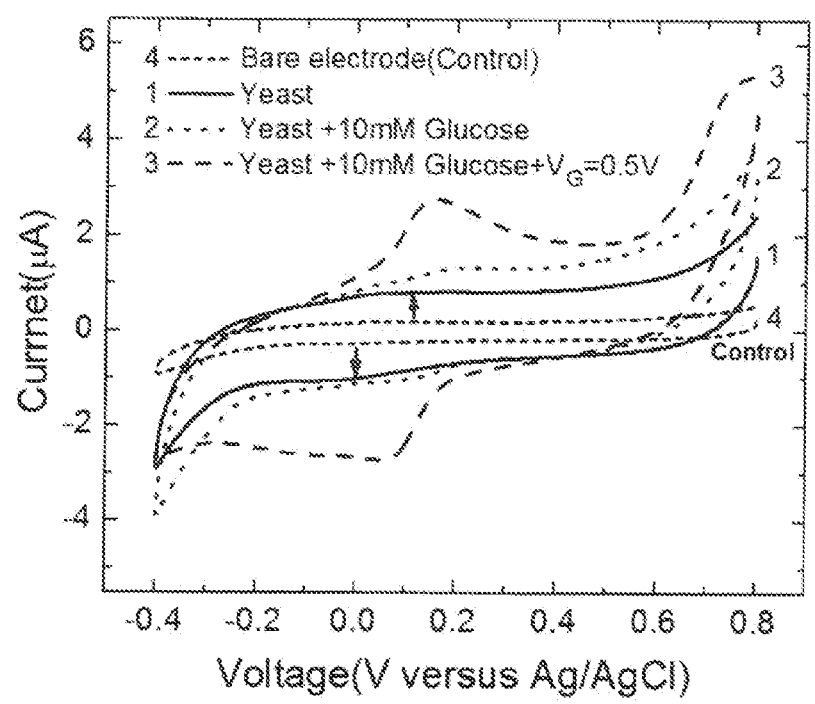
FIG. 5 is a set of cyclic voltammograms (CVs) obtained to test the system of FIG. 1. A yeast-immobilized graphite working electrode was exposed to a glucose solution under different conditions to generate CVs depicted as CVs 1, 2, and 3. CV1 show a control current in just PBS solution. CV2, obtained in a glucose solution, shows an increased anodic current due to the oxidation of glucose by yeast. CV3 shows a further increased oxidation current caused by application of positive $V_G$. CV4 was obtained with a bare working electrode in either PBS or a glucose solution.

Cyclic voltammetry of glucose was performed using the system shown in FIG. 1 and as described in Example 1 to show the oxidation of glucose by the immobilized yeast. The cyclic voltammograms (CVs) in FIG. 5 were obtained using the yeast-immobilized graphite electrode exposed to a glucose solution under different conditions.

CV1 was obtained in phosphate buffered saline (PBS) whereas CV 2 was obtained with glucose added to the PBS. CV 1 shows a pair of weak redox peaks indicated by the arrows with a formal potential at 50 mV vs. an Ag/AgCl reference electrode. Comparing CV2 with CV1 shows increased anodic current, indicating the oxidation of glucose by the yeast. CV3 shows further increase in the oxidation current and enhanced redox peaks caused by the application of a positive $V_G$. CV4 was obtained with a bare working electrode in PBS and subsequently with glucose added to the PBS.

Example 3: Glucose Concentration Monitoring with Different $V_G$ Values

A more direct way of showing the oxidation of glucose is to use the system 100 described in FIG. 1 and Example 1 to monitor the change in the glucose concentration of samples for different values of $V_G$. Samples of glucose with a volume of 2 mL in phosphate buffered saline (PBS, 26.8 mM, 2 mL) were processed at room temperature using yeast-immobilized electrodes at $V_{cell}$=0.6 V vs. Ag/AgCl for a total time of 1200 s. Aliquots of 5 μL were taken from the processed samples every 300 s to be measured using commercial glucose test strips and a glucose meter, whose measuring range is 20-600 mg/dL (1.11-33.33 mM). The samples were tested at room temperature.

PBS was prepared using de-ionized water (18.2 MΩ-cm). All measurements were made with PBS at room temperature. BREEZE®2 blood glucose test strips and a BREEZE®2 blood glucose meter (Bayer Health Care, Mishawaka, Wis.) with a measuring range of 20-600 mg/dL (1.11-33.33 mM) were used to measure the concentration of glucose in samples.

With reference to FIG. 6(a), the curves show the $V_G$-dependent change in glucose concentration under the aerobic condition. The curves were obtained with yeast-immobilized electrodes prepared under identical conditions. Curve1, obtained with $V_G$=0 V, shows a gradual decease in glucose concentration spanning the 1200 s period. The effect of a positive $V_G$ appears to be causing faster decreases in glucose concentration. As $V_G$ was increased, the decrease in glucose concentration occurred at progressively faster rates as indicated by Curves 2-4. When the polarity of $V_G$ was reversed, the rate became progressively slower than that of Curve1 as indicated by Curves 5-7. Curve 8 is the control trace obtained using a bare electrode, showing no change in glucose concentration. The depletion of glucose is presumably to be due to the metabolism in yeast.

With reference to FIG. 6(b), similar curves were obtained under the anaerobic condition (achieved by purging solution with dry $N_2$ for 1 hour) as shown in FIG. 6(a). Comparing the glucose depletion curves in FIGS. 6(a) and 6(b) shows that the anaerobic process shows faster depletion rates than those for the aerobic case. This effect is consistent with the fact that the rate of glucose consumption is higher under anaerobic conditions than that observed under aerobic conditions due to the fact that the anaerobic process is associated with a low energy yield.

Example 4: SEM Image of Immobilized Yeast on Working Electrode

Figure 7:
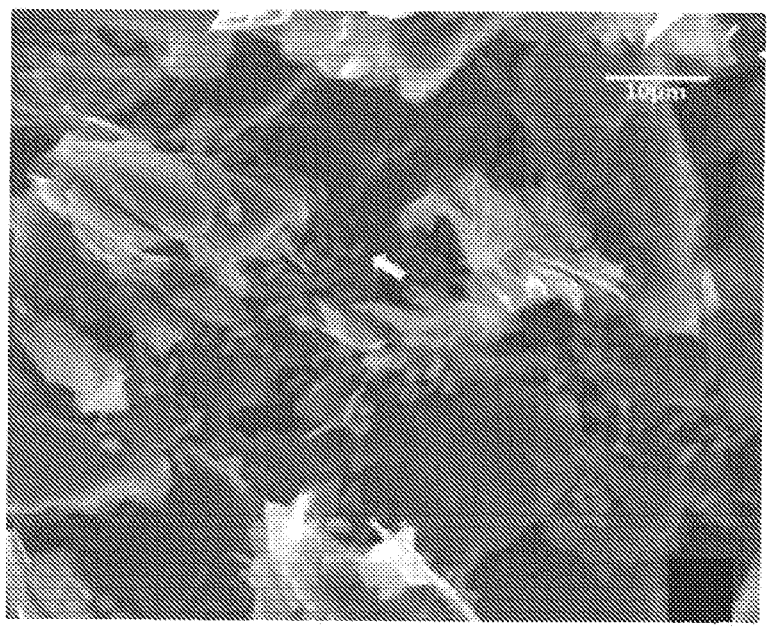
FIG. 7 is a scanning electron microscopy (SEM) image of a selected area of a yeast-immobilized electrode before electrochemical processing where yeast cells are indicated by the arrow.

The measurements conducted on system 100 and as described in Example 1 were carried out in the lag phase of yeast budding (2-10 hours) to avoid yeast reproduction. With reference to FIG. 7, a scanning electron microscopy (SEM) image shows a selected area of an electrode before carrying out the electrochemical processing of a glucose sample.

The field emission scanning electron microscope used to image the immobilized yeast on electrodes was made by Hitachi (FE-SEM 5000). The 3 μm×1 μm grain-like structures are yeast cells. SEM images of the same area after 120 min of electrochemical processing in glucose (image not shown) appear to be identical to the one in FIG. 7, suggesting that the faster depletion of glucose was not caused by yeast reproduction.

Example 5: Probing End Products of Glucose Metabolism—ATP (Aerobic)

To provide further evidence for the presumed glucose metabolism, the end products of the typical metabolic processes were probed. Aerobic metabolism of glucose is the dismantlement of glucose by glycolysis, Krebs cycle and the electron carriers' traversing the electron-transport chain in the presence of oxygen.

Adenosine triphosphate (ATP) is synthesized during metabolism. Luminescence assay of ATP in yeast cells suspended in glucose samples, which were electrochemically processed using the system 100 described in FIG. 1 as described above, was performed to reveal the ATP produced as a function of $V_G$. The assay of ATP was performed using the BacTiter-Glo™ Microbial Cell Viability Assay kit (Promega, Madison, Wis.). The luminescence was detected using a Victor3 Multilabel Plate Counter (Perkin Elmer) and displayed as relative light units (RLU).

Figure 8:
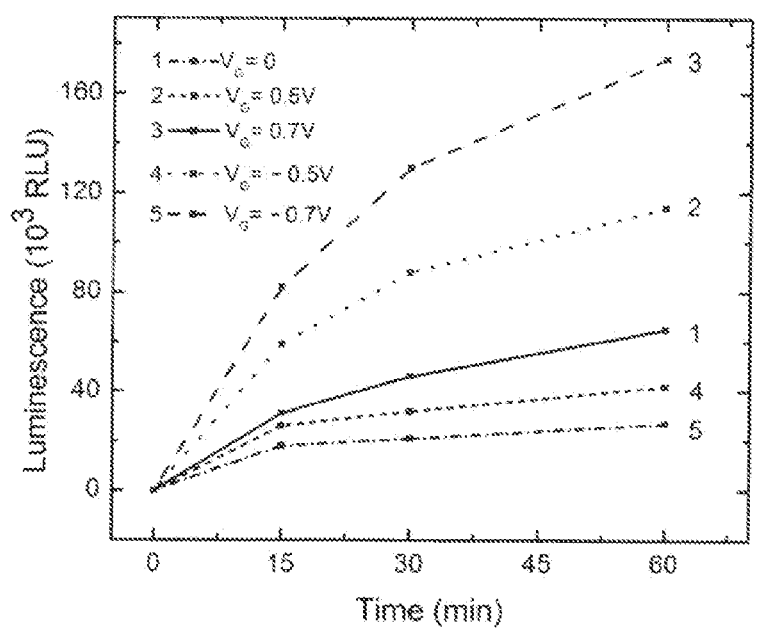
FIG. 8 is a graph of Luminescence ($\times 10^3$ RLU) v. time (s) obtained using a spectrophotometer with samples processed on the system of FIG. 1 under aerobic conditions. The graph shows the $V_G$-controlled production of an end product of glucose metabolism, adenosine triphosphate (ATP), with and without $V_G$ at different times during a 1-hour period at room temperature.

FIG. 8 shows, under the aerobic condition, the amounts of ATP present in the yeast cells at different times of a 60-min processing period for different $V_G$ values. The curves in Figure FIG. 8 show that, as $V_G$ became more positive, increasing amounts of ATP were produced, whereas the amount of ATP progressively decreased for negative $V_G$ values. The ATP production is to be compared with the glucose consumption shown in FIG. 6(a) to show the correlation between the two $V_G$-dependent processes. This correlation is non-accidental since metabolism of glucose produces ATP.

Example 6: Probing End Products of Glucose Metabolism—ATP (Anaerobic)

Under the anaerobic condition, glucose metabolism in yeast proceeds via the fermentation pathway with the formation of ATP, ethanol and carbon dioxide ($CO_2$) as the end products.

Figure 9:
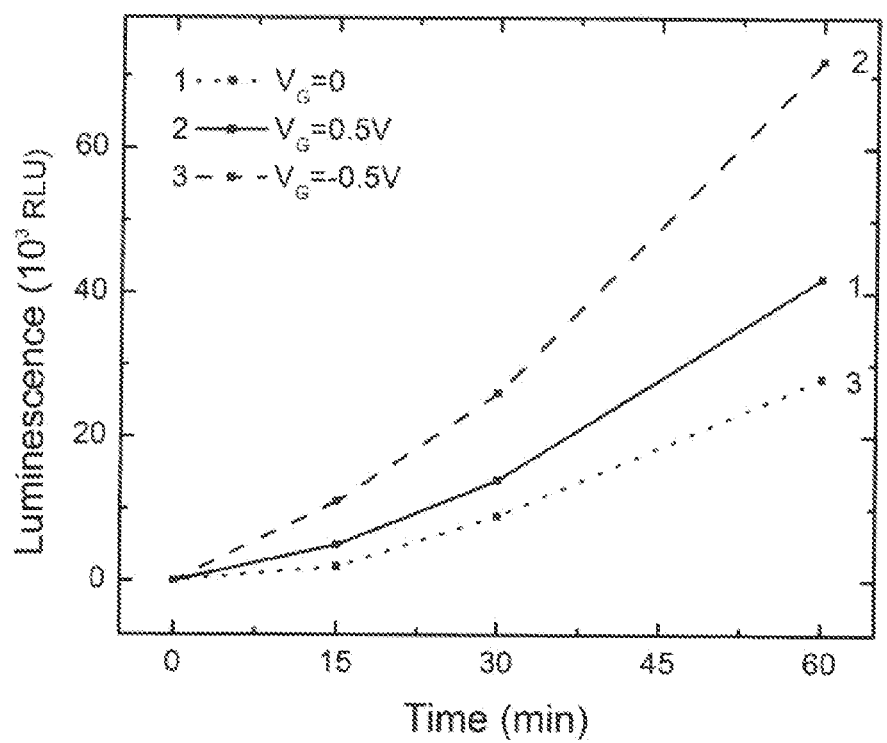
FIG. 9 is a graph of Luminescence ($\times 10^3$ RLU) v. time (s) obtained using a spectrophotometer with samples processed on the system of FIG. 1 under anaerobic conditions. The graph shows the $V_G$-controlled production of an end product of glucose metabolism, ATP, with and without $V_G$ at different times over a 1-hour period at room temperature.

FIG. 9 shows the ATP production under anaerobic conditions. Curve 1, which shows the ATP amount obtained with $V_G$=0, is much less than the corresponding Curve 1 in the aerobic case (see FIG. 8). This difference is consistent with the fact that, for yeast, the ATP produced in the aerobic environment is 1.4-5.4 times per mole of glucose more than that produced in the anaerobic case. Curve 2 and Curve 3 were obtained with a positive and a negative $V_G$, respectively. The effects of the polarity of $V_G$ on the production of ATP as indicated by the three curves are consistent with those for the aerobic case.

Example 7: Probing End Products of Glucose Metabolism—Ethanol (Anaerobic)

Figure 10:
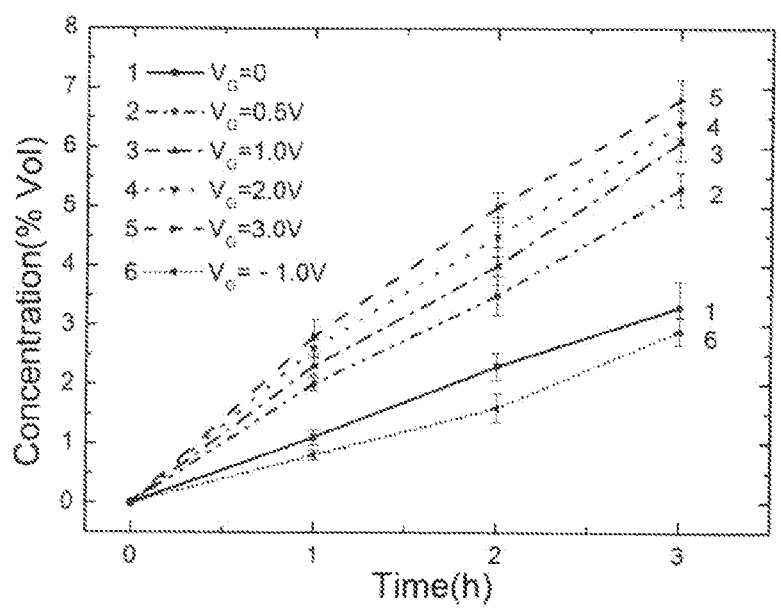
FIG. 10 shows graphs of ethanol concentration (% v/v) v. time (h) obtained on the system of FIG. 1 by ebulliometry of electrochemically processed glucose samples using the system of FIG. 1 under anaerobic conditions. The graphs show the $V_G$-controlled generation of an end product of glucose metabolism, ethanol, with and without $V_G$ at different times during a 3-hour period at room temperature.

Ebulliometry of electrochemically processed glucose samples using the system 100 described in FIG. 1 was performed to monitor the generation of ethanol. The curves in FIG. 10 show the generation of ethanol by fermentation occurring in 100 mM glucose samples (30 mL) with and without $V_G$ at different times during a 3-hour period at room temperature. The curves show that positive $V_G$ led faster production of ethanol.

The ethanol concentration of samples (% v/v) was measured using an ebulliometer (Dujardin-Salleron, Paris, France) at room temperature. The working electrode was a 10 mm v 10 mm carbon cloth.

Example 8: Probing End Products of Glucose Metabolism—$CO_2$ (Anaerobic)

Figure 11:
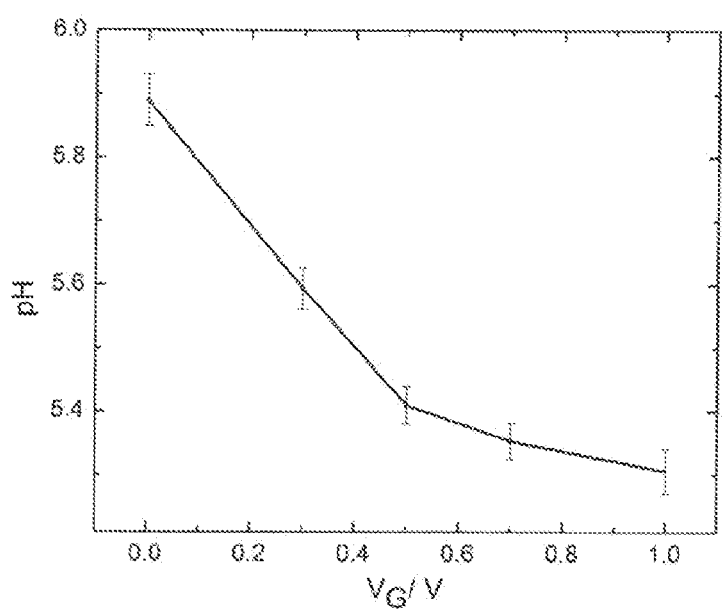
FIG. 11 is a graph of pH v. $V_G$ (V) obtained on the system of FIG. 1 under anaerobic conditions. The graph shows $V_G$-induced changes in the pH of electrochemically processed 100 mM glucose samples at the end of a 1-hour period. The decrease in pH shown is attributed to the formation of an end product of glucose metabolism, $CO_2$. The curve was obtained at room temperature.

Measured using a pH meter, the curve in FIG. 11 shows the $V_G$-induced changes in the pH of electrochemically processed 100 mM glucose samples at the end of a 1-hour period. The pH of the samples decreased from 5.9 to 5.3 as $V_G$ was increased from 0 V to 1 V. It is known that $CO_2$ dissolves slightly in water to form a weak acid, $H_2CO_3$. The decrease in pH is attributed to the increase in the metabolically produced $CO_2$ content in the samples.

Example 9: Short Time Production of Ethanol by Fermentation—Only Gating and Working Electrode (No Current Involved in Production)

The system 100 according to the second exemplary embodiment was used to probe the production of ethanol production (similar to Example 7). This system 100 includes the electric circuit between the one or more gating electrodes 110 and the working electrode 102, however forgoes the other electrodes normally found in a conventional three electrode cell (the reference electrode 104 and counter electrode 106). The electrochemical system was turned off. The system 100 according to the second exemplary embodiment is able to control the formation of end products in a metabolic reaction without a current being involved in their production.

Figure 12:
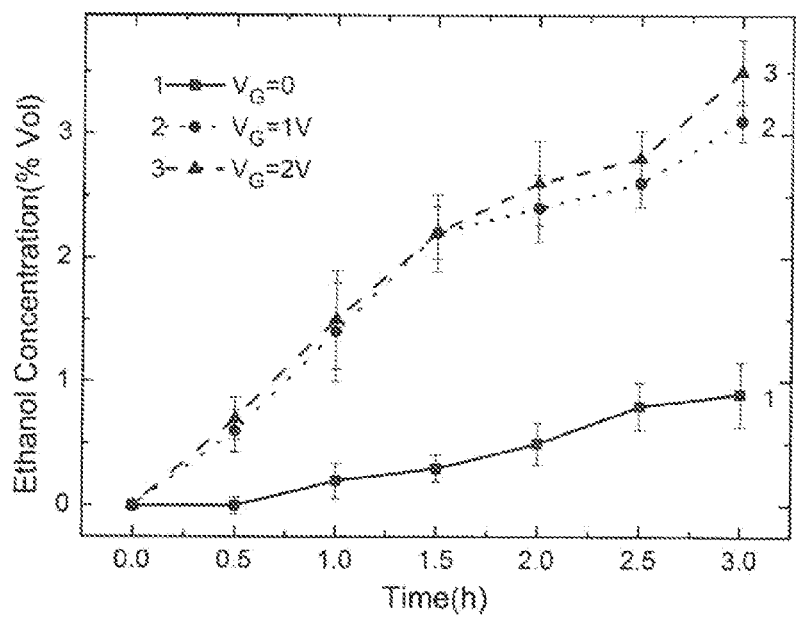
FIG. 12 is a graph of ethanol concentration (% v/v) v. time (h) obtained with glucose samples processed on a modified version of the system of FIG. 1 including only the working electrode and the gating electrode and the voltage source that generates $V_G$. The graph shows $V_G$-controlled production of ethanol by fermentation over a 3-hour period. The curves were obtained at room temperature.

With reference to FIG. 12, an applied gating voltage $V_G$ of 1V significantly increased the rate of ethanol production by fermentation of 30 mL of a 26.6 mM glucose solution by yeast cells. An applied gating voltage $V_G$ of 2V produced similar results as 1V. The measurements were made at room temperature under anaerobic condition. The working electrode was a 10 mm×10 mm carbon cloth.

Example 10: Short Time Depletion of Glucose Due to Fermentation—Only Gating and Working Electrode (No Current Involved in Production)

The system 100 according to the second exemplary embodiment was used to monitor glucose concentration (similar to Example 3). This system 100 includes the electric circuit between the one or more gating electrodes 110 and the working electrode 102, however forgoes the other electrodes normally found in a conventional three electrode cell (the reference electrode 104 and counter electrode 106). The system 100 according to the second exemplary embodiment is able to control the formation of end products in a metabolic reaction without a current being involved in their production.

Figure 13:
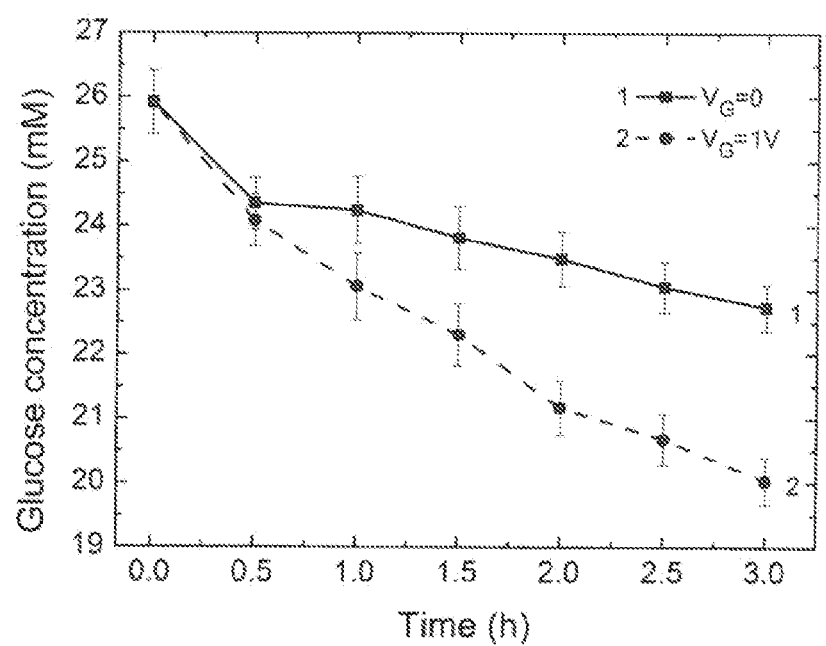
FIG. 13 is a graph of glucose concentration (mM) v. time (h) obtained with electrochemically processed glucose samples processed on a modified version of the system of FIG. 1 including only the working electrode and the gating electrode and the voltage source that generates $V_G$. The graph shows consumption of glucose concentration at an increased rate as $V_G$ is increased over a 3-hour period. The curves were obtained at room temperature.

The glucose concentration measurements in FIG. 13 were made using the same solutions used in Example 9. The increased rate of production of ethanol in FIG. 12 correlates with the increased rate of glucose depletion in a 30 mL solution shown in FIG. 13 at varying levels of $V_G$. The measurements were made at room temperature. The working electrode was a 10 mm×10 mm carbon cloth. This confirms that ethanol is being produced by the fermentation of glucose in yeast cells.

Figure 14:
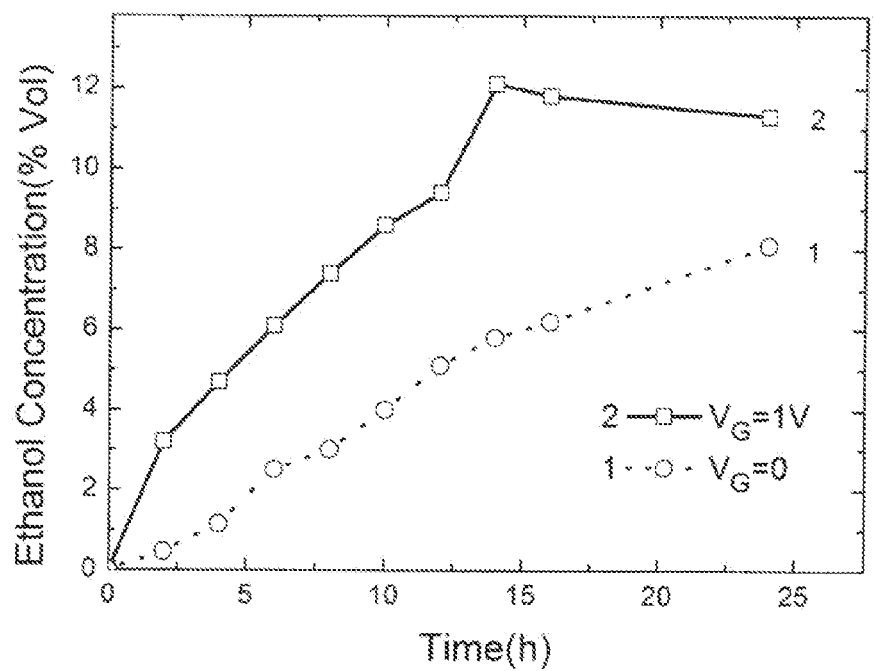
FIG. 14 is a graph of ethanol concentration (% v/v) v. time (h) obtained with electrochemically processed glucose samples processed on the system of FIG. 1 according to the first exemplary embodiment under anaerobic conditions. The graph shows an increase and then plateau of ethanol production by fermentation as $V_G$ is applied over 28 hours. The curves were obtained at room temperature.

Example 11: Ethanol Production by Fermentation (Anaerobic Metabolism of Glucose) Over 28 Hours With reference to FIG. 14, ethanol was produced using the system 100 according to the first exemplary embodiment as described in Example 1. This system 100 includes the conventional three-electrode cell and a plurality of gating electrodes as illustrated in FIG. 1. An applied $V_G$ of 3V increased the rate of ethanol formation over the entire 28 hour period as compared to the rate with $V_G=0$ V. The increased rate of metabolism under $V_G=3V$ plateaued at approximately 11 hours. The volume of glucose solution was 250 mL and the starting glucose concentration was 1.6 M. The concentration of yeast used was 5 gram/L. The fermentation was carried out at 30° C. under anaerobic condition. A 7 cm×13 cm carbon cloth was used as the working electrode. The yeast was cultivated as described in Example 1. Alternatively, yeast can be mixed with water and glucose without cultivation for immediate fermentation process and similar fermentation results were obtained.

Figure 15:
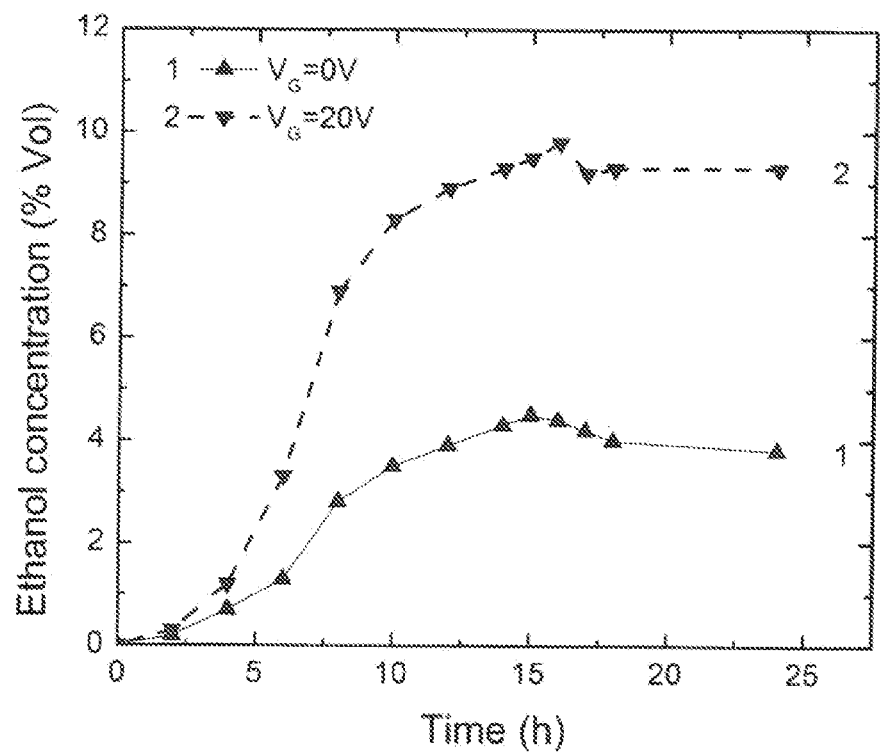
FIG. 15 is a graph of ethanol concentration (% v/v) v. time (h) obtained with electrochemically processed glucose samples processed on the system of FIG. 1 according to the second exemplary embodiment under anaerobic conditions. The graph shows an increase and then plateau of ethanol production by fermentation as $V_G$ is applied over 24 hours. The curves were obtained at room temperature.

Example 12: Ethanol Production by Fermentation (Anaerobic Metabolism of Glucose) Over 24 Hours Using a Two-Electrode System With reference to FIG. 15, ethanol was produced using the system 100 according to the second exemplary embodiment (See FIG. 2). As described in Example 1, a piece of 0.5 mm-diameter copper wire coated with a thin layer of insulator (enamel) was used as the gating (second) electrode. This system is able to control the formation of ethanol by fermentation of glucose without a current being involved in its production.

An applied $V_G$ of 20 V increased the rate of ethanol formation over the entire 24 hour period as compared to the rate with $V_G=0$ V. The increased rate of fermentation under $V_G=20$ V plateaued at approximately 14 hours. The volume of glucose solution was 250 mL and the starting glucose concentration was 200 g/L. The concentration of yeast used was 12 gram/L. The fermentation was carried out at 30° C. under anaerobic condition. A 7 cm×13 cm carbon cloth was used as the working electrode and a copper wire coated with enamel was used as the gating electrode. Dry yeast was mixed with water and glucose and the mixture was used immediately for the fermentation process without cultivation. Alternatively, dry yeast can be cultivated first as described in Example 1. During the fermentation process, yeast was suspended in the mixture in the presence of the gating electrodes and working electrode. No attempt was made to immobilize yeast on the electrodes.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing operation of the invention, the inventors are not bound by theories described herein. The invention is not limited to the exact details shown and described, for variations obvious to one skilled in the art will be included within the invention defined by the claims.

The invention claimed is:

1. A method for voltage controlled metabolism in a two electrode electrostatic bio-reactive cell, comprising:
   providing an electrode system consisting of a first electrode and a second electrode;
   suspending at least one organism and at least one metabolic substrate that can be metabolized by the organism in a solution in contact with the electrode system, wherein one or both electrodes are coated with an insulator so that no current flows in the circuit;
   applying a gating voltage $V_G$ between the first electrode and the second electrode disposed within the solution; and
   controlling a rate of a metabolic reaction caused by the at least one organism by selecting at least one of the magnitude and polarity of the applied gating voltage $V_G$.

2. The method of claim 1, wherein the organism is yeast.

3. The method of claim 1, wherein the organism is algae.

4. The method of claim 1, wherein the metabolic substrate is a sugar.

5. The method according to claim 1, wherein the gating voltage $V_G$ changes the rate of the metabolic reaction.

6. The method of claim 1, wherein the metabolic substrate is metabolized to ethanol by the organism.

7. The method of claim 1, wherein the method further comprises the step of collecting useful end products from the organism.

8. The method of claim 7, wherein the useful end products comprise biofuels.

9. The method of claim 7, wherein the useful end products comprise proteins, antibodies, or enzymes.

10. The method of claim 1, wherein the organism is a photosynthetic organism.

11. The method according to claim 1, wherein the gating voltage $V_G$ changes the rate of growth of the organism.

* * * * *